(12) United States Patent
Eickmeier et al.

(10) Patent No.: US 6,323,207 B1
(45) Date of Patent: *Nov. 27, 2001

(54) BENZOYLGUANIDINE DERIVATIVES

(75) Inventors: Christian Eickmeier, Wiesbaden; Erich Buerger, Bingen; Stefan Matthias Blech, Warthausen; Otto Roos, deceased, late of Schwabenheim, all of (DE), by Winnifried Charlotte Friederike Roos, legal representative

(73) Assignee: Boehringer Ingelheim Pharma KG, Ingelheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/396,704

(22) Filed: Sep. 15, 1999

Related U.S. Application Data

(60) Provisional application No. 60/109,386, filed on Nov. 23, 1998.

(30) Foreign Application Priority Data

Sep. 22, 1998 (DE) .............................. 198 43 489

(51) Int. Cl.$^7$ ...................... A61K 31/495; A61K 31/496; C07D 401/06; C07D 403/06; C07D 405/06
(52) U.S. Cl. ................................. 514/253.13; 514/254.01; 514/254.1; 514/255.01; 544/360; 544/372; 544/379; 544/391
(58) Field of Search ..................................... 544/372, 391, 544/360, 379; 514/252, 255, 253.13, 254.01, 254.1, 255.01

(56) References Cited

U.S. PATENT DOCUMENTS 5,292,755 * 3/1994 Englert et al. ........................ 514/331
6,114,335 * 9/2000 Buerger et al. ................. 514/252.13

FOREIGN PATENT DOCUMENTS

97/26253 * 7/1997 (WO) .

* cited by examiner

Primary Examiner—Emily Bernhardt
(74) Attorney, Agent, or Firm—R. P. Raymond; T. X. Witkowski; A. R. Stempel

(57) ABSTRACT

Novel benzoylguanidine derivatives of general formula I

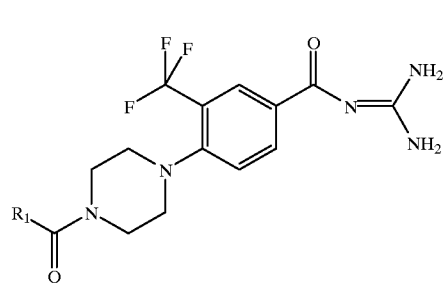

(I)

useful for the treatment or reduction of tissue damage due to ischaemia.

20 Claims, No Drawings

BENZOYLGUANIDINE DERIVATIVES

RELATED APPLICATIONS

Benefit of U.S. Provisional Application Ser. No. 60/109,386, filed on Nov. 23, 1998 is hereby claimed.

FIELD OF THE INVENTION

The present invention relates to novel benzoylguanidine derivatives, methods for producing these compounds, and their use as pharmaceuticals.

DESCRIPTION OF THE INVENTION

In its first aspect the invention provides novel benzoylguanidine derivatives of the formula I

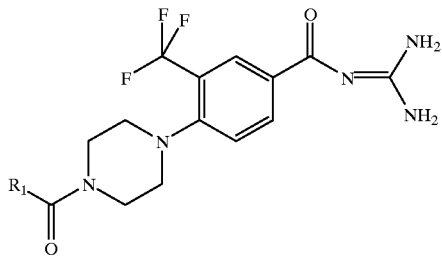

(I)

wherein $R_1$ denotes $C_{1-8}$-alkyl,
  heteroaryl unsubstituted or mono- or polysubstituted by a branched or unbranched $C_{1-4}$-alkyl group, a cycloalkyl group, a branched or unbranched $C_{1-4}$-alkoxy group, an $NH_2$ group or a primary or secondary amino group, a trifluoromethyl group, a cyano or nitro group or halogen,
  aryl unsubstituted or mono- or polysubstituted by a branched or unbranched $C_{1-4}$-alkyl group, a branched or unbranched $C_{1-4}$-alkoxy group, an $NH_2$ group or a primary or secondary amino group, a trifluoromethyl group, a hydroxy, cyano or nitro group or halogen or by a 5- or 6-membered heteroaryl group which may contain one, two, three, four or five heteroatoms selected from nitrogen, oxygen and sulphur—identical to one another or different—
  alkylaryl, unsubstituted or mono- or polysubstituted in the aryl and/or alkyl partial structure by a branched or unbranched $C_{1-4}$-alkyl group, a branched or unbranched $C_{1-4}$-alkoxy group, an $NH_2$ group or a primary or secondary amino group, a trifluoromethyl group, a cyano or nitro group or halogen.

The invention also includes tautomers of compounds of the formula I, and pharmaceutically acceptable salts thereof.

The preferred compounds for the purposes of the present invention are the compounds of general formula I wherein $R_1$ may denote an unsubstituted phenyl ring or a phenyl ring which is substituted by fluorine or by a methyl, trifluoromethyl, methoxy group or by a pyrrolyl group, or

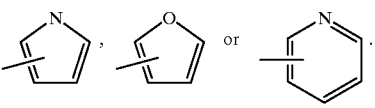

The following compounds are particularly preferred:
4-(4-(2-Pyrrolylcarbonyl)-1-piperazinyl)-3-trifluoromethyl-benzoylguanidine methanesulphonate

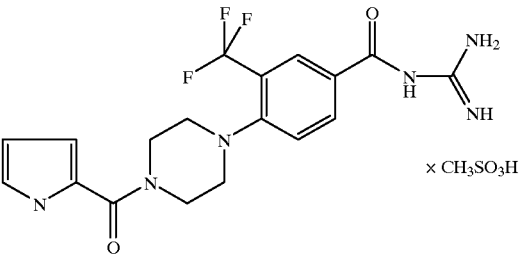

and
4-(4-(4-Fluorophenylcarbonyl)-1-piperazinyl)-3-trifluoromethyl-benzoylguanidine methanesulphonate

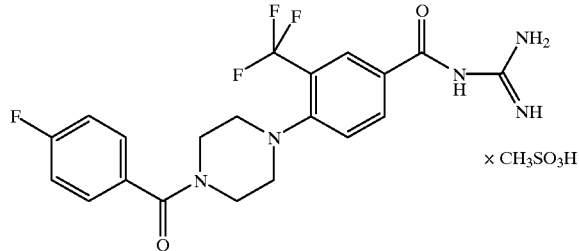

$C_{1-4}$-alkyl or $C_{1-8}$-alkyl generally denotes a branched or unbranched hydrocarbon group having 1 to 4 or 8 carbon atoms, which may optionally be substituted by one or more halogen atoms, preferably fluorine, which may be identical to or different from one another. The following hydrocarbon groups are mentioned by way of example:
  methyl, ethyl, propyl, 1-methylethyl (isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1- ethyl-1-methylpropyl and 1-ethyl-2-methylpropyl. Unless otherwise stated, the preferred hydrocarbon groups are lower alkyl groups having 1 to 4 carbon atoms such as methyl, ethyl, propyl, iso-propyl, n-butyl, 1-methylpropyl, 2-methylpropyl or 1,1-dimethylethyl.

Alkoxy generally denotes a straight-chained or branched alkyl group bound via an oxygen atom. A lower alkoxy group having 1 to 4 carbon atoms is preferred. The methoxy group is particularly preferred.

Aryl generally denotes an aromatic group having 6 to 10 carbon atoms—including compositions in which the aromatic group may be substituted by one or more lower alkyl groups, trifluoromethyl groups, cyano groups, alkoxy groups, nitro groups, amino groups and/or one or more halogen atoms, which may be identical or different; the preferred aryl group is an optionally substituted phenyl group, whilst the preferred substituents are halogen, such as fluorine, chlorine or bromine, cyano and hydroxyl; for the purposes of the present invention fluorine is the preferred halogen. The aryl substituent—preferably phenyl—may moreover be substituted with a 5- or 6-membered heteroaryl group which may contain one, two, three, four or five heteroatoms from the group comprising nitrogen, oxygen and sulphur, and again the substituents may be identical or different.

Aralkyl generally denotes an aryl group having 7 to 14 carbon atoms bound via an alkylene chain, the aromatic group optionally being substituted by one or more lower alkyl groups, alkoxy groups, nitro groups, amino groups and/or one or more halogen atoms, the substituents being identical or different. Aralkyl groups having 1 to 6 carbon atoms in the aliphatic moiety and 6 carbon atoms in the aromatic moiety are preferred.

The preferred aralkyl groups—unless otherwise stated—are benzyl, phenethyl and phenylpropyl.

Halogen, unless otherwise stated—denotes fluorine, chlorine, bromine and iodine, preferably fluorine, chlorine or bromine.

Unless otherwise specified, amino denotes an $NH_2$ function which may optionally be substituted by one or two $C_{1-8}$-alkyl, aryl or aralkyl groups, which may be identical or different.

Accordingly, alkylamino denotes for example methylamino, ethylamino, propylamino, 1-methyleneethylamino, butylamino, 1-methylpropylamino, 2-methylpropylamino or 1,1-dimethylethylamino.

Correspondingly, dialkylamino denotes, for example, dimethylamino, diethylamino, dipropylamino, dibutylamino, di-(1-methylethyl)amino, di-(1-methylpropyl)amino, di-2-methylpropylamino, ethylmethylamino, methylpropylamino.

Cycloalkyl generally denotes a saturated or unsaturated cyclic hydrocarbon group having 5 to 9 carbon atoms which may optionally be substituted by a halogen atom or a number of halogen atoms—preferably fluorine—which may be identical to or different from one another. Cyclic hydrocarbon groups having 3 to 6 carbon atoms are preferred. Examples include cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl and cyclononinyl.

Heteroaryl for the purposes of the above definition generally denotes a 5- to 6-membered ring which may contain oxygen, sulphur and/or nitrogen as heteroatoms and to which another aromatic ring may be fused. 5- and 6-membered aromatic rings which contain an oxygen, a sulphur and/or up to two nitrogen atoms and which are optionally benzo-condensed are preferred.

Examples of particular heterocyclic systems include: acridinyl, acridonyl, alkylpyridinyl, anthraquinonyl, ascorbyl, azaazulenyl, azabenzanthracenyl, azabenzanthrenyl, azachrysenyl, azacyclazinyl, azaindolyl, azanaphthacenyl, azanaphthalenyl, azaprenyl, azatriphenylenyl, azepinyl, azinoindolyl, azinopyrrolyl, benzacridinyl, benzazapinyl, benzofuryl, benzonaphthyridinyl, benzopyranonyl, benzopyranyl, benzopyronyl, benzoquinolinyl, benzoquinolizinyl, benzothiepinyl, benzothiophenyl, benzylisoquinolinyl, bipyridinyl, butyrolactonyl, caprolactamyl, carbazolyl, carbolinyl, catechinyl, chromenopyronyl, chromonopyranyl, cumarinyl, cumaronyl, decahydroquinolinyl, decahydroquinolonyl, diazaanthracenyl, diazaphenanthrenyl, dibenzazapinyl, dibenzofuranyl, dibenzothiphenyl, dichromylenyl, dihydrofuranyl, dihydroisocumarinyl, dihydroisoquinolinyl, dihydropyranyl, dihydropyridinyl, dihydropyridonyl, dihydropyronyl, dihydrothiopyranyl, diprylenyl, dioxanthylenyl, oenantholactamyl, flavanyl, flavonyl, fluoranyl, fluoresceinyl, furandionyl, furanochromanyl, furanonyl, fiuranoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiochromenyl, hydrothiophenyl, indolizidinyl, indolizinyl, indolonyl, isatinyl, isatogenyl, isobenzofurandionyl, isobenzfuranyl, isochromanyl, isoflavonyl, isoindolinyl, isoindolobenzazapinyl, isoindolyl, isoquinolinyl, isoquinuclidinyl, lactamyl, lactonyl, maleimidyl, monoazabenzonaphthenyl, naphthalenyl, naphthimidazopyridindionyl, naphthindolizinedionyl, naphthodihydropyranyl, naphthofuranyl, naphthyridinyl, oxepinyl, oxindolyl, oxolenyl, perhydroazolopyridinyl, perhydroindolyl, phenanthraquinonyl, phthalideisoquinolinyl, phthalimidyl, phthalonyl, piperidinyl, piperidonyl, prolinyl, parazinyl, pyranoazinyl, pyranoazolyl, pyranopyrandionyl, pyranopyridinyl, pyranoquinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolidinyl, pyrrolizidinyl, pyrrolizinyl, pyrrolodioazinyl, pyrrolonyl, pyrrolopyrimidinyl, pyrroloquinolonyl, pyrrolyl, quinacridonyl, quinolinyl, quinolizidinyl, quinolizinyl, quinolonyl, quinuclidinyl, rhodaminyl, spirocumaranyl, succinimidyl, sulpholanyl, sulpholenyl, tetrahydrofuranyl, tetrahydroisoquinolinyl, tetrahydropyranyl, tetrahydropyridinyl, tetrahydrothiapyranyl, tetrahydrothiophenyl, tetrahydrothipyranonyl, tetrahydrothipyranyl, tetronyl, thiaphenyl, thiachromanyl, thiadecalinyl, thianaphthenyl, thiapyranyl, thiapyronyl, thiazolopyridinyl, thienopyridinyl, thienopyrrolyl, thienothiophenyl, thiepinyl, thiochromenyl, thiocumarinyl, thiopyranyl, triazaanthracenyl, triazinoindolyl, triazolopyridinyl, tropanyl, xanthenyl, xanthonyl, xathydrolyl, adeninyl, alloxanyl, alloxazinyl, anthranilyl, azabenzanthrenyl, azabenzonaphthenyl, azanaphthacenyl, azaphenoxazinyl, azapurinyl, azinyl, azoloazinyl, azolyl, barbituric acid, benzazinyl, benzimidazolethionyl, benzimidazolonyl, benzisothiazolyl, benzisoxazolyl, benzocinnolinyl, benzodiazocinyl, benzodioxolanyl; benzodioxolyl, benzopyridazinyl, benzothiazepinyl, benzothiazinyl, benzothiazolyl, benzoxazinyl, benzoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxanyl, dioxenyl, dioxepinyl, dioxinonyl, dioxolanyl, dioxolonyl, dioxopiperazinyl, dipyrimidopyrazinyl, dithiolanyl, dithiolenyl, dithiolyl, flavinyl, furopyrimidinyl, glycocyamidinyl, guaninyl, hexahydropyrazinoisoquinolinyl, hexahydropyridazinyl, hydantoinyl, hydroimidazolyl, hydroparazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, methylthyminyl, methyluracilyl, morpholinyl, naphthimidazolyl, oroticyl, oxathianyl, oxathiolanyl, oxazinonyl, oxazolidinonyl, oxazolidinyl, oxazolidonyl, oxazolinonyl, oxazolinyl, oxazolonyl, oxazolopyrimidinyl, oxazolyl, perhydrocinnolinyl, perhydropyrroloazinyl, perhydropyrrolothiazinyl, perhydrothiazinonyl, perimidinyl, phenazinyl, phenothiazinyl, phenoxathiinyl, phenoxazinyl, phenoxazonyl, phthalazinyl, piperazindionyl, piperazinodionyl, polyquinoxalinyl, pteridinyl, pterinyl, purinyl, pyrazinyl, pyrazolidinyl, pyrazolidonyl, pyrazolinonyl, parazolinyl, pyrazolobenzodiazepinyl, pyrazolonyl, pyrazolopyrimidinyl, pyrazolotriazinyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenzodiazepinyl, pyrrolodiazinyl, pyrrolopyrimidinyl, quinazolidinyl, quinazolinonyl, quinazolinyl, quinoxalinyl, sultamyl, sultinyl, sultonyl, tetrahydrooxazolyl, tetrahydropyrazinyl, tetrahydropyridazinyl, tetrahydroquinoxalinyl, tetrahydrothiazolyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, thyminyl, triazolopyrimidinyl, uracilyl, xanthinyl, xylitolyl, azabenzonaphththenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, pentazinyl, polyoxadiazolyl, sydonyl, tetraoxanyl, tetrazepinyl, tetrazinyl, tetrazolyl, thiadiazinyl, thiadiazolinyl, thiadiazolyl, thiadioxazinyl, thiatriazinyl, thiatriazolyl, thiatriazolyl, triazepinyl, triazinoindolyl, triazinyl, triazolinedionyl, triazolinyl, triazolyl, trioxanyl, triphenodioxazinyl, triphenodithiazinyl, trithiadiazepinyl, trithianyl or trioxolanyl.

Compounds of this type are already known from German Offenlegungsschrift 196 01 303.8.

As a result of their effect as inhibitors of cellular $Na^+/H^+$ exchange, such compounds may be used as active ingredients of pharmaceutical compositions or they may be used as intermediate products for the preparation of such active ingredients. The compounds according to the invention are effective against arrhythmias which occur in hypoxia, for example. They can also be used for diseases connected with ischaemia (such as cardiac, cerebral, gastrointestinal—such as mesenterial thrombosis/embolism, pulmonary, renal ischaemia, ischaemia of the liver, ischaemia of the skeletal muscle). Such diseases include for example coronary heart disease, cardiac infarct, angina pectoris, stable angina pectoris, ventricular arrhythmias, sub-ventricular arrhythmias, cardiac insufficiency—and also in support of bypass operations, for supporting open heart surgery, for supporting operations which require the blood supply to the heart to be interrupted and for supporting heart transplants—embolism in the pulmonary circulation, acute or chronic kidney failure, chronic kidney insufficiency, cerebral infarct, reperfusion damage caused by the resumption of blood supply to areas of the brain after the clearing of vascular occlusions and acute and chronic bleeding disorders in the brain. Here, the compounds mentioned may also be used in conjunction with thrombolytic agents such as t-PA, streptokinase and urokinase.

During reperfusion of the ischaemic heart (e.g. after an attack of angina pectoris or cardiac infarct) irreversible damage may occur to cardiomyocytes in the affected region. The compounds according to the invention have a cardioprotective activity, inter alia, in such cases.

The prevention of damage to transplants must also be included under the heading of ischaemia (e.g. for protecting the transplant such as the liver, kidney, heart or lung, before, during and after implantation and during storage of the organs for transplant), which may occur in connection with transplants. The compounds are also drugs with a protective effect during angioplastic surgery on the heart and on the peripheral blood vessels.

In essential hypertension and diabetic nephropathy the cellular sodium proton exchange is increased. The compounds according to the invention are therefore suitable as inhibitors of this exchange in order to prevent these diseases.

The compounds according to the invention are further characterised by a powerful inhibitory effect on the proliferation of cells. Consequently, the compounds are useful drugs in the treatment of diseases in which cell proliferation plays a primary or secondary role and may be used as drugs against cancers, benign tumours or for example prostate hypertrophy, atherosclerosis, organ hypertrophy and hyperplasia, fibrotic diseases and late complications of diabetes.

Moreover, compounds of this type are known to have a favorable effect on the blood levels of the serum lipoproteins.

It has now been found that, surprisingly, the compounds of general formula I have the advantage over the benzoylguanidine derivatives already known from the prior art, of not only being unexpectedly more effective but also being suitable for oral administration.

The active substances according to general formula I may be used as an aqueous injectable solution (e.g. for intravenous, intramuscular or subcutaneous administration), as tablets, suppositories, ointments, as plasters for transdermal application, as aerosols for inhalation through the lungs or as a nasal spray.

The content of active substance in a tablet or suppository is between 5 and 200 mg, preferably between 10 and 50 mg. For inhalation, the individual dose is between 0.05 and 20 mg, preferably between 0.2 and 5 mg. For parenteral injection, the single dose is 30 between 0.1 and 50 mg, preferably between 0.5 and 20 mg. The above doses may be administered several times a day if necessary.

The following are some examples of pharmaceutical preparations containing the active substance:

Tablets

| | |
|---|---|
| Active substance of general formula I | 20.0 mg |
| Magnesium stearate | 1.0 mg |
| Corn starch | 62.0 mg |
| Lactose | 83.0 mg |
| Polyvinylpyrrolidone | 1.6 mg |

Solution for Injection

The solution may be sterilised by standard methods.

| | |
|---|---|
| Active substance of general formula I | 0.9 g |
| Sodium chloride | 0.3 g |
| Water for injection | ad 100 ml |

Aqueous Solution for Nasal Administration or Inhalation

| | |
|---|---|
| Active substance of general formula I | 0.3 g |
| Sodium chloride | 0.9 g |
| Benzalkonium chloride | 0.01 mg |
| Purified water | ad 100 ml |

The above solution is suitable for nasal administration in a spray or, when used in conjunction with a device which produces an aerosol having a particle size of preferably between 2 and 6 μm, it is suitable for administration into the lungs.

Capsules for Inhalation

The compounds of general formula I are packed into hard gelatin capsules in micronised form (particle size essentially between 2 and 6 μM), optionally with the addition of micronised carrier substances such as lactose. They are inhaled by means of conventional devices for powder inhalation. Between 0.2 and 20 mg of the active substance of general formula I and 0 to 40 mg of lactose are packed into each capsule, for example.

Aerosol for Inhalation

| | |
|---|---|
| Active substance of general formula I | 1 part |
| Soya lecithin | 0.2 parts |
| Propellant gas mixture | ad 100 parts |

The preparation is preferably transferred into aerosol containers with a metering valve, each spray delivering a dose of 0.5 mg. For other dosages in the range specified, preparations containing a larger or smaller proportion of active substance are conveniently used.

Ointment (composition g/100 g of ointment)

| | |
|---|---|
| Active substance of general formula I | 2 g |
| Fuming hydrochloric acid | 0.011 g |
| Sodium pyrosulphite | 0.05 g |
| Mixture of equal parts of cetyl alcohol and stearyl alcohol | 20 g |
| White Vaseline | 5 g |
| Artificial bergamot oil | 0.075 g |
| Distilled water | ad 100 |

The ingredients are processed in the usual way to form an ointment.

The methods of producing the compounds according to the invention are generally known from the prior art; thus, the compounds according to the invention may be obtained by the following method, for example:

By reacting 4-(1-piperazinyl)-3-trifluoromethylbenzoic acid esters of general formula II

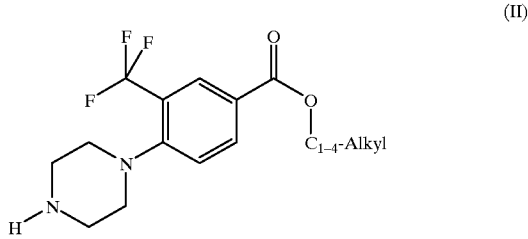

(II)

with a compound of general formula III $$R_1C(O)Q$$ (III)

wherein Q denotes a leaving group which may be substituted by the piperazine nitrogen, optionally in the presence of adjuvants, preferably carbonyldiimidazole, the resulting benzoic acid derivative of general formula IV

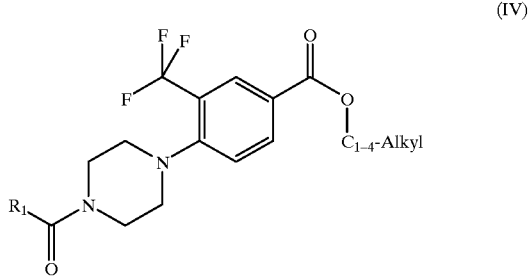

(IV)

is obtained, which is suspended in a suitable, preferably anhydrous, solvent, preferably dimethylformamide, and is mixed with a mixture of a solution or suspension of a base—preferably sodium hydride in a suitable anhydrous solvent—preferably dimethylformamide—with a guanidine salt—preferably guanidine hydrochloride—and the reaction product is isolated.

The present invention is illustrated by the Examples which follow:

EXAMPLES

Methyl 4-fluoro-3-trifluoromethyl-benzoate 35.4 g (170 mmol) of 4-fluoro-3-(trifluoromethyl)-benzoic acid in 250 ml of methanol are mixed with 68 ml of $SOCl_2$, whilst cooling with ice, at 5° C. within 25 minutes. After it has all been added, the reaction mixture is refluxed for a further 3 hours. The reaction solution is cooled to ambient temperature and evaporated down in vacuo. The oily residue is taken up in 200 ml of diethylether and extracted with water, saturated $NaHCO_3$ solution and again with water. The combined organic phases are dried over magnesium sulphate and evaporated down in vacuo.

Yield: 29.0 g (77%)

Methyl 4-(4-benzyl-1-piperazinyl)-3-trifluoromethyl-benzoate 7 g (31.5 mmol) of methyl 4-fluoro-3-trifluoromethyl-benzoate are dissolved in 60 ml of dry dimethylsulphoxide (DMSO) and combined with 5.55 g (31.5 mmol) of N-benzylpiperazine and 4.35 g (31.5 mmol) of potassium carbonate. The mixture is stirred for 12 hours at 90° C. After cooling, the reaction mixture is poured into 200 ml of water and extracted three times with ethyl acetate. The combined organic phases are washed with water and saturated sodium chloride solution, dried over magnesium sulphate and distilled off in vacuo. The residue is chromatographed on silica gel with a mixture of ethyl acetate and n-heptane.

Yield: 3.93 g (33%)

Methyl 4-(1-piperazinyl)-3-trifluoromethyl-benzoate 20.2 g (53.3 mmol) of methyl 4-(4-benzyl-1-piperazinyl)-3-trifluoromethyl-benzoate are dissolved in 200 ml of methanol and combined with 2 g of palladium on charcoal and hydrogenated over a period of 1.4 hours at 70° C. under a hydrogen pressure of 5 bar. The solution is suction filtered over CELITE® filter agent and distilled off in vacuo.

Yield: 14.85 g (97%)

General method of coupling methyl 4-(1-piperazinyl)-3-trifluoromethyl-benzoate with benzoic acids:

5 mmol of the corresponding carboxylic acid are dissolved in 30 ml of absolute tetrahydrofuran (THF) and combined under protective gas at 0° C. with 810 mg (5 mmol) of carbonyldiimidazole and stirred for 2 hours at ambient temperature (about 25° C.). Then 1.44 g (5 mmol) of methyl 4-(1-piperazinyl)-3-trifluoromethyl-benzoate are added and the mixture is stirred for about another 12 hours. The solution is evaporated to dryness in vacuo and taken up in ethyl acetate. After washing with saturated $NaHCO_3$ solution, saturated NaCl solution and water, the organic phases are dried over $MgSO_4$ and evaporated down in vacuo. After crystallisation in a suitable solvent or chromatography on silica gel with a suitable eluant, the following compounds are obtained.

1. methyl 4-(4-(3-methoxyphenylcarbonyl)-1-piperazinyl)-3-trifluoromethyl-benzoate
   Column chromatography: ethyl acetate/n-heptane (2:1)
   Yield: 81%
2. methyl 4-(4-(2-pyrrolylcarbonyl)-1-piperazinyl)-3-trifluoromethyl-benzoate
   Crystallised from methanol
   Yield: 75%
   Melting point: 149° C.
3. methyl 4-(4-(4-fluorophenylcarbonyl)-1-piperazinyl)-3-trifluoromethyl-benzoate
   Column chromatography: ethyl acetate/n-heptane (2:1)
   Yield: 77%
4. methyl 4-(4-(2-methoxyphenylcarbonyl)-1-piperazinyl)-3-trifluoromethyl-benzoate
   Column chromatography: ethyl acetate/n-heptane (2:1)
   Yield: 79%
5. methyl 4-(4-(3-trifluoromethylphenylcarbonyl)-1-piperazinyl)-3-trifluoromethyl-benzoate
   Column chromatography: ethyl acetate/n-heptane (2:1)
   Yield: 83%
6. methyl 4-(4-phenylcarbonyl-1-piperazinyl)-3-trifluoromethyl-benzoate
   Column chromatography: ethyl acetate/n-heptane (2:1)
   Yield: 87%
7. methyl 4-(4-(2-furylcarbonyl)-1-piperazinyl)-3-trifluoromethyl-benzoate
   Column chromatography: ethyl acetate/n-heptane (2:1)
   Yield: 75%
8. methyl 4-(4-(3-methylphenylcarbonyl)-1-piperazinyl)-3-trifluoromethyl-benzoate
   Column chromatography: ethyl acetate/n-heptane (2:1)
   Yield: 79%
9. methyl 4-(4-(4-(1-pyrryl)phenylcarbonyl)-1-piperazinyl)-3-trifluoromethyl-benzoate
   Column chromatography: ethyl acetate/n-heptane (2:1)
   Yield: 87%
10. methyl 4-(4-(2-pyridylcarbonyl)-1-piperazinyl)-3-trifluoromethyl-benzoate
    Column chromatography: ethyl acetate/n-heptane (2:1)
    Yield: 73%

General method for preparing acyl guanidines from the corresponding methyl carbonates:

5.09 g (127.2 mmol) of 60% NaH in white oil is washed twice with ether and decanted off. 200 ml of absolute DMF are added and 12.15 g (127.2 mmol) of guanidine hydrochloride are added in small amounts with stirring under protective gas. After stirring for 1 hour, 21.2 mmol of the corresponding methyl ester are added and the solution is stirred for a further 2 hours at a temperature of about 120° C. The reaction mixture is then allowed to cool to ambient temperature, filtered and the filtrate is evaporated down in vacuo. After chromatography on silica gel with a suitable eluant and conversion with ethereal hydrochloric acid or other pharmacologically acceptable acids into the corresponding salts, the following compounds are obtained:

1st Example 4-(4-(4-Methoxyphenylcarbonyl)-1-piperazinyl)-3-trifluoromethyl-benzoylguanidine-hydrochloride

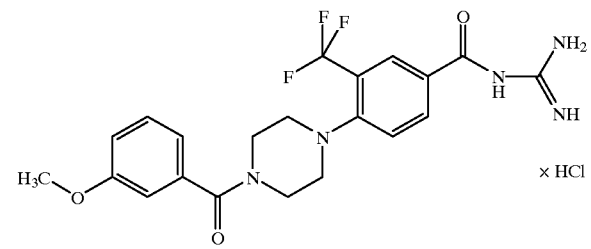

from methyl 4-(4-(3-methoxyphenylcarbonyl)-1-piperazinyl)-3-trifluoromethyl-benzoate Column chromatography: ethyl acetate/methanol (5:1);

Yield: 71%;

Melting point: >200° C.;

MS: $(M+H)^+$=450 (free base).

2nd Example 4-(4-(2-Pyrrolylcarbonyl)-1-piperazinyl)-3-trifluoromethyl-benzoylguanidine-methanesulphonate

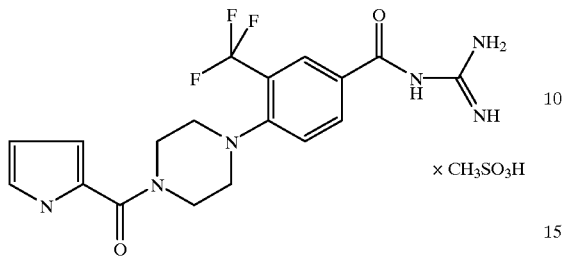

from methyl 4-(4-(2-pyrrolylcarbonyl)-1-piperazinyl)-3-trifluoromethyl-benzoate
  Column chromatography: ethyl acetate/methanol (5:1);
  Yield: 66%;
  Melting point: 246° C.;
  MS: (M+H)⁺=409 (free base).

3rd Example 4-(4-(4-Fluorophenylcarbonyl)-1-piperazinyl)-3-trifluoromethyl-benzoylguanidine-methanesulphonate

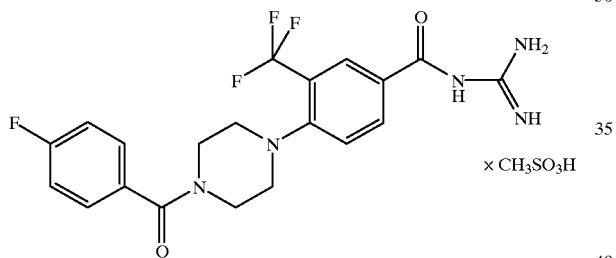

from methyl 4-(4-(4-fluorophenylcarbonyl)-1-piperazinyl)-3-trifluoromethyl-benzoate
  Column chromatography: ethyl acetate/methanol (5:1);
  Yield: 40%;
  Melting point: 140° C.;
  MS: (M+H)⁺=438 (free base).

4th Example 4-(4-(2-Methoxyphenylcarbonyl)-1-piperazinyl)-3-trifluoromethyl-benzoylguanidine-hydrochloride

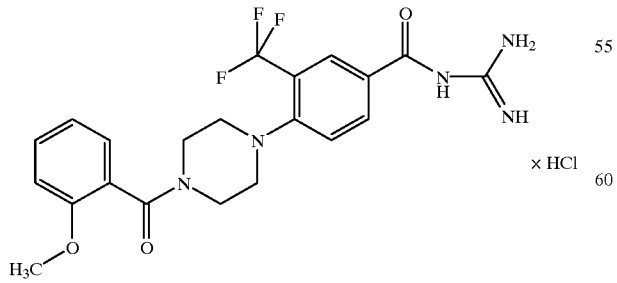

from methyl 4-(4-(2-methoxyphenylcarbonyl)-1-piperazinyl)-3-trifluoromethyl-benzoate
  Column chromatography: ethyl acetate/methanol (5:1);
  Yield: 71%;
  Melting point: 219° C. (decomposition);
  MS: (M+H)⁺=450 (free base).

5th Example 4-(4-(3-Trifluoromethylphenylcarbonyl)-1-piperazinyl)-3-trifluoromethyl-benzoylguanidine-hydrochloride

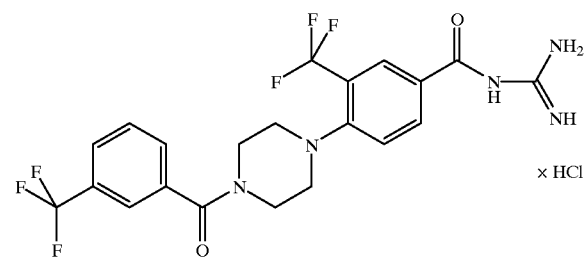

from methyl 4-(4-(3-trifluoromethylphenylcarbonyl)-1-piperazinyl)-3-trifluoromethyl-benzoate
  Column chromatography: ethyl acetate/methanol (5:1);
  Yield: 25%;
  Melting point: 140° C. (decomposition);
  MS: (M+H)⁺=488 (free base).

6th Example 4-(4-Phenylcarbonyl-1-piperazinyl)-3-trifluoromethyl-benzoylguanidine-hydrochloride

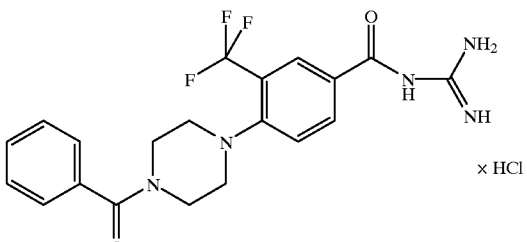

from methyl 4-(4-phenylcarbonyl-1-piperazinyl)-3-trifluoromethyl-benzoate
  Column chromatography: ethyl acetate/methanol (5:1);
  Yield: 64%;
  Melting point: 214° C.;
  MS: (M+H)⁺=420 (free base).

7th Example 4-(4-(2-Furylcarbonyl)-1-piperazinyl)-3-trifluoromethyl-benzoylguanidine-methanesulphonate

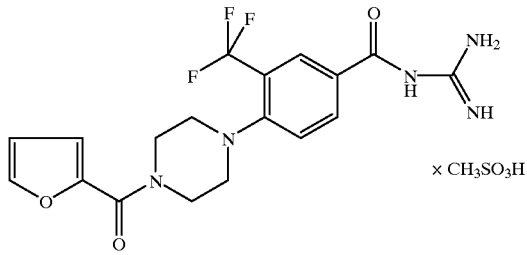

from methyl 4-(4-(2-furylcarbonyl)-1-piperazinyl)-3-trifluoromethyl-benzoate
Crystallisation from ether;
Yield: 19%;
Melting point: 190° C. (decomposition);
MS: (M+H)$^+$=410 (free base).

8th Example 4-(4-(3-Methylphenylcarbonyl)-1-piperazinyl)-3-trifluoromethyl-benzoylguanidine-methanesulphonate

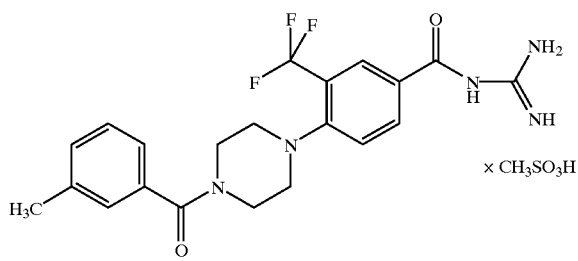

from methyl 4-(4-(3-methylphenylcarbonyl)-1-piperazinyl)-3-trifluoromethyl-benzoate
Crystallisation from methanol/ethyl acetate;
Yield: 76%;
Melting point: 199° C.;
MS: (M+H)$^+$=434 (free base).

9th Example 4-(4-(4-(1-Pyrrolyl)phenylcarbonyl)-1-piperazinyl)-3-trifluoromethyl-benzoylguanidine-dimethylsulphonate

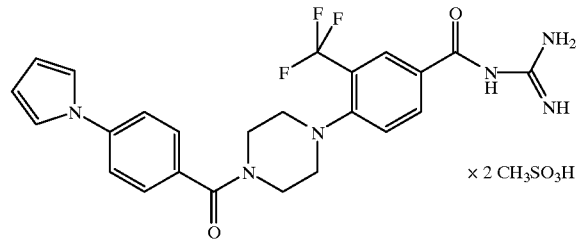

from methyl 4-(4-(4-(1-pyrryl)phenylcarbonyl)-1-piperazinyl)-3-trifluoromethyl-benzoate
Crystallisation from methanol;
Yield: 48%;
Melting point: 150° C. (decomposition);
MS: (M+H)$^+$=485 (free base).

10th Example 4-(4-(2-Pyridylcarbonyl)-1-piperazinyl)-3-trifluoromethyl-benzoylguanidine-dimethanesulphonate

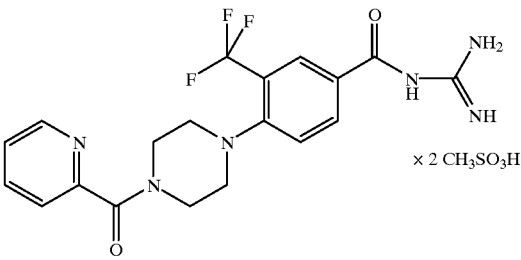

from methyl 4-(4-(2-pyridylcarbonyl)-1-piperazinyl)-3-trifluoromethyl-benzoate
Column chromatography: ethyl acetate/methanol (5:1);
Yield: 34%;
Melting point: 115° C. (decomposition);
MS: (M+H)$^+$=421 (free base).

Pharmacological Data

Inhibition of the Na$^+$/H$^+$ exchanger in human intestinal cancer cells (HT-29):

HT-29 cells are incubated in growth medium at 37° C. with 5% CO$_2$. After 3–5 days the growth medium was removed, the cells were washed and charged with 7.5 $\mu$M of BCECF-AM (pH-sensitive fluorescent dye) at 37° C. without CO$_2$. After 30 minutes the cells were washed and acidified with the following medium: 70 mM choline chloride, 20 mM NH$_4$Cl, 1 mM MgCl$_2$, 1.8 mM CaCl$_2$, 5 mM glucose and 15 mM HEPES, pH 7.5.

After 6 minutes' incubation at 37° C. without CO$_2$ the cells are washed, and incubated for 5 minutes with wash medium: 120 mM choline chloride, 5 mM KCl, 1 mM MgCl$_2$, 1.8 mM CaCl$_2$, 5 mM glucose and 15 mM MOPS, pH 7.0.

The wash medium is removed and control medium is added with or without the test compound: 120 mM NaCl, 5 mM KCl, 1 mM MgCl$_2$, 1.8 mM CaCl$_2$, 5mM glucose, 15 mM MOPS, pH 7.0.

The cells are incubated for 4 minutes at 37° C. without CO$_2$ and measured fluorimetrically (CytoFluor 2350). The fluorescence of the dye BCECF is measured at the excitation wavelengths 485 nm (pH sensitive) and 440 nm (non-pH sensitive) and at the emission wavelength 530 nm. The cytoplasmic pH is calculated from the ratio of fluorescences at 485 and 440 nm. The fluorescence ratio is calibrated by measuring the fluorescent signal after equilibration of external and internal pH with nigericin.

| Example | IC$_{50}$/10$^{-6}$ mol l$^{-1}$ |
|---|---|
| 1 | 0.076 |
| 3 | 0.038 |
| 4 | 0.084 |
| 5 | 0.023 |

-continued

| Example | IC$_{50}$/10$^{-6}$ mol l$^{-1}$ |
|---|---|
| 7 | 0.084 |
| 8 | 0.061 |
| 10 | 0.079 |

The compounds according to the invention also surprisingly have very good bioavailability and long half-lives after oral administration—properties which make them exceptionally suitable for oral use.

Pharmacokinetic data:

Male rats weighing about 200 g (not starved) were used for the tests. For intravenous and oral administration the substances are dissolved in an acidified aqueous solution (pH 3).

Individual bolus injections (0.5 mg/kg i.v., 2.5 mg/kg p.o.) are injected into the caudal vein (0.2 ml/200 g) or administered through a canular into the stomach (1 ml/200 g). The solutions administered are analysed to confirm the dosage given. 0.5 ml aliquots of blood are taken from the retroorbital venous plexus under brief halothane anaesthesia with heparinised glass capillaries according to the following plan:

after i.v. administration: 5 min, 15 min, 30 min, 1 h, 2 h, 4 h, 6 h, 8 h;

after oral administration: 15 min, 1 h, 2 h, 4 h, 6 h, 8 h, 24 h, 32 h.

The samples are centrifuged and the plasma is stored at −20° C. until ready to be analysed. Preparation of the samples is carried out by liquid-liquid extraction with an internal standard. The plasma extracts are analysed by reversed phase HPLC, coupled with an electrospray tandem mass spectrometer.

The pharmacokinetic data is determined from the corresponding plasma concentrations by compartment-free analysis using the TopFit program (Heinzel, G., Woloszczak, R., Thomann, P. TopFit 2.0—Pharmacokinetic and pharmacodynamic data analysis, system for the PC, Gustav Fischer Verlag, Stuttgart, Jena, New York, 1993).

| Example | F | t½ (i.v.) | t½ (p.o.) |
|---|---|---|---|
| 2 | 63 | 1.3 | 5.0 |
| 3 | 71 | 3.1 | 5.4 |
| 5 | 58 | 5.4 | 7.5 |

What is claimed is:

1. A compound of the formula I

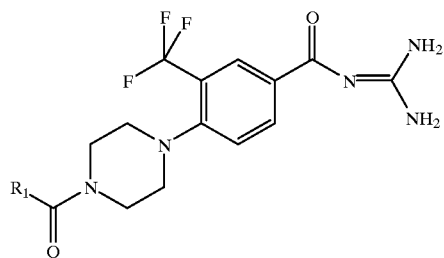

(I)

wherein:

R$_1$ is a C$_{1-8}$-alkyl group,
aryl unsubstituted or mono- or polysubstituted by a branched or unbranched C$_{1-4}$-alkyl group, a branched or unbranched C$_{1-4}$-alkoxy group, an NH$_2$ group optionally substituted by one or two identical or different C$_{1-8}$-alkyl, aryl, or aralkyl groups, a trifluoromethyl group, a hydroxy, cyano, or nitro group or halogen, or -alkylaryl, unsubstituted or mono- or polysubstituted in the aryl and/or alkyl partial structure by a branched or unbranched C$_{1-4}$-alkyl group, a branched or unbranched C$_{1-4}$-alkoxy group, an NH$_2$ group optionally substituted by one or two identical or different C$_{1-8}$-alkyl, aryl, or aralkyl groups, a trifluoromethyl group, a cyano, or nitro group or halogen, or a tautomer or pharmaceutically acceptable salt thereof.

2. A compound of the formula I

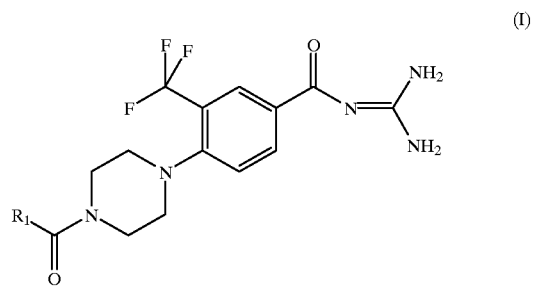

(I)

wherein:

R$_1$ is an unsubstituted phenyl ring or a phenyl ring substituted by a fluorine atom or by a methyl, trifluoromethyl, methoxy group, or pyrrolyl group; or is one of the following groups:

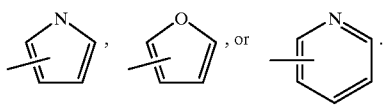

or a tautomer or pharmaceutically acceptable salt thereof.

3. 4-(4-(2-Pyrrolylcarbonyl)-1-piperazinyl)-3-trifluoromethyl-benzoylguanidine-methanesulphonate or a tautomer or pharmaceutically acceptable salt thereof.

4. 4-(4-(4-Fluorophenylcarbonyl)-1-piperazinyl)-3-trifluoromethyl-benzoylguanidine-methanesulphonate or a tautomer or pharmaceutically acceptable salt thereof.

5. A process for preparing a compound of general formula I

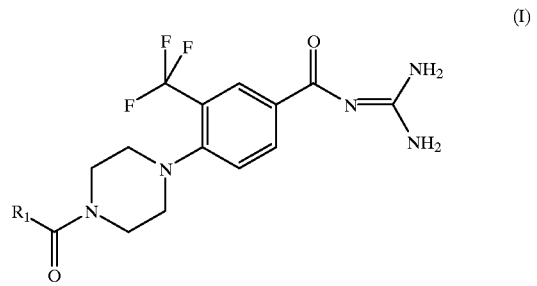

(I)

wherein a 4-(1-piperazinyl)-3-trifluoromethylbenzoic acid ester of the formula II

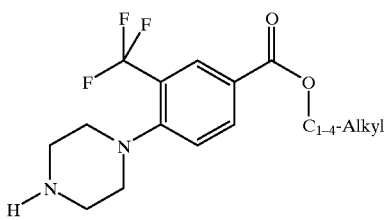

is reacted with a compound of the formula III $$R_1C(O)Q \tag{III}$$

wherein Q is a leaving group, optionally in the presence of carbonyldiimidazole, and the resulting benzoic acid derivative of the formula IV

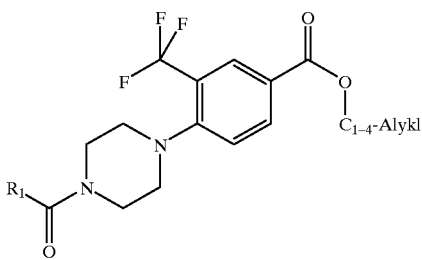

is suspended in a suitable solvent, and is mixed with a mixture of a solution or suspension of a base with a guanidine salt and the reaction product is isolated, wherein:

$R_1$ is a $C_{1-8}$-alkyl group, aryl unsubstituted or mono- or polysubstituted by a branched or unbranched $C_{1-4}$-alkyl group, a branched or unbranched $C_{1-4}$-alkoxy group, an $NH_2$ group optionally substituted by one or two identical or different $C_{1-8}$-alkyl, aryl, or aralkyl groups, a trifluoromethyl group, a hydroxy, cyano, or nitro group, or halogen, or -alkylaryl, unsubstituted or mono- or polysubstituted in the aryl and/or alkyl partial structure by a branched or unbranched $C_{1-4}$-alkyl group, a branched or unbranched $C_{1-4}$-alkoxy group, an $NH_2$ group optionally substituted by one or two identical or different $C_{1-8}$-alkyl, aryl, or aralkyl groups, a trifluoromethyl group, a cyano, or nitro group, or halogen.

6. A pharmaceutical preparation comprising a compound of the formula I, in accordance with one of claims 1, 2, 3, or 4, and a pharmaceutically acceptable carrier.

7. A method for the treatment or reduction of tissue damage due to ischaemia which comprises administering to a host suffering from ischaemia a therapeutic amount of a compound of the formula I, in accordance with one of claims 1, 2, 3, or 4.

8. The method according to claim 5, wherein the base is sodium hydride.

9. The method according to claim 8, wherein the sodium hydride is in an anhydrous solvent.

10. The method according to claim 9, wherein the anhydrous solvent is dimethylformamide.

11. The method according to claim 5, wherein the base is in an anhydrous solvent.

12. The method according to claim 11, wherein the anhydrous solvent is dimethylformamide.

13. The method according to claim 5, wherein the guanidine salt is guanidine hydrochloride.

14. The method according to claim 5, wherein:

$R_1$ is an unsubstituted phenyl ring or a phenyl ring substituted by a fluorine atom or by a methyl, trifluoromethyl, methoxy group, or pyrrolyl group; or is one of the following groups:

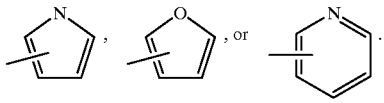

15. The method according to claim 14, wherein the base is sodium hydride.

16. The method according to claim 15, wherein the sodium hydride is in an anhydrous solvent.

17. The method according to claim 16, wherein the anhydrous solvent is dimethylformamide.

18. The method according to claim 14, wherein the base is in an anhydrous solvent.

19. The method according to claim 18, wherein the anhydrous solvent is dimethylformamide.

20. The method according to claim 14, wherein the guanidine salt is guanidine hydrochloride.

* * * * *